(12) United States Patent
Chen et al.

(10) Patent No.: US 8,933,196 B2
(45) Date of Patent: Jan. 13, 2015

(54) PEPTIDE CHROMATOGRAPHIC PURIFICATION ASSISTED BY COMBINING OF SOLUBILITY PARAMETER AND SOLUTION CONFORMATION ENERGY CALCULATIONS

(75) Inventors: Wen-Yih Chen, Taoyuan (TW);
Li-Chiao Chang, Tainan (TW);
Ruoh-Chyu Ruaan, Taoyuan (TW);
Ching-Wei Tsai, Taoyuan (TW)

(73) Assignees: National Central University, Jhongli, Taoyuan (TW); Scinopharm Taiwan Ltd., Shan-Hua, Tainan (TW)

( * ) Notice: Subject to any disclaimer, the term of this patent is extended or adjusted under 35 U.S.C. 154(b) by 350 days.

(21) Appl. No.: 13/472,152

(22) Filed: May 15, 2012

(65) Prior Publication Data

US 2012/0296068 A1    Nov. 22, 2012

Related U.S. Application Data

(60) Provisional application No. 61/488,387, filed on May 20, 2011, provisional application No. 61/600,004, filed on Feb. 17, 2012.

(51) Int. Cl.
*C07K 1/14*    (2006.01)
*C07K 1/20*    (2006.01)

(52) U.S. Cl.
CPC .................................... *C07K 1/20* (2013.01)
USPC ....................................................... 530/344

(58) Field of Classification Search
None
See application file for complete search history.

(56) References Cited

U.S. PATENT DOCUMENTS 5,076,909 A        12/1991   Overfield et al.
2006/0150716 A1 *  7/2006    Yoshioka et al. ............ 73/61.51

FOREIGN PATENT DOCUMENTS

| JP | 1207257 A | | 8/1989 |
| JP | 1207257 A | * | 8/1989 |
| JP | 3227996 A | | 10/1991 |
| JP | 2000/005598 A | | 1/2000 |

OTHER PUBLICATIONS

Totsune et al (Hypertension, 1994, 24: 758-762).*

* cited by examiner

*Primary Examiner* — Sean Aeder
(74) *Attorney, Agent, or Firm* — Enshan Hong; Kent H. Cheng; VLP Law Group LLP

(57) ABSTRACT

A method of purifying a compound from a mixture through a chromatographic column loaded with a column adsorbent. The method comprises:
applying the mixture to the chromatographic column;
eluting the mixture with an elution solvent composition; and
collecting the compound;
wherein at least one of the column adsorbent and elution solvent is selected based on one of solubility parameters of the compound, column adsorbent, elution solvent, and conformation energy of the compound.

11 Claims, 8 Drawing Sheets

SEQUENCE LISTING

```
<160> NUMBER OF SEQ ID NOS: 6

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<223> OTHER INFORMATION: C-term NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (11)..(11)
<223> OTHER INFORMATION: D-amino acid
<220> FEATURE:
<223> OTHER INFORMATION: C-term NH2

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
```

```
<220> FEATURE:
<221> NAME/KEY: MOD_RES
<222> LOCATION: (32)..(32)
<223> OTHER INFORMATION: D-amino acid
<220> FEATURE:
<223> OTHER INFORMATION: C-term NH2

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (39)..(39)
<223> OTHER INFORMATION: D-amino acid
<220> FEATURE:
<223> OTHER INFORMATION: C-term NH2

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Leu Ala Arg Glu Leu Glu Glu Leu Asn
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-amino acid

<400> SEQUENCE: 6

Leu Ala Leu Ala Arg Glu Leu Glu Glu Leu Asn
1               5                   10
```

PEPTIDE CHROMATOGRAPHIC PURIFICATION ASSISTED BY COMBINING OF SOLUBILITY PARAMETER AND SOLUTION CONFORMATION ENERGY CALCULATIONS

RELATED APPLICATIONS

This application claims priority from U.S. Provisional Patent Application Ser. No. 61/488,387, which was filed on May 20, 2011, and U.S. Provisional Patent Application Ser. No. 61/600,004, which was filed on Feb. 17, 2012. The entire content of these two provisional applications is incorporated herein as reference.

SEQUENCE LISTING

The instant application contains a Sequence Listing which has been submitted electronically in ASCII format and is hereby incorporated by reference in its entirety. Said ASCII copy, created on Sep. 11, 2014, is named 4951-130_SL.txt and is 3,367 bytes in size.

BACKGROUND OF THE INVENTION

1. Field of the Invention

The present application relates to identifying, quantifying, or purifying a compound from a mixture via a chromatographic technique, in particular gel-based chromatographic purification of a peptide compound.

2. Description of the Related Art

Chromatography (RPLC) is widely used for analysis of various chemical substances. Most purification schemes rely on the understanding of physico-chemical properties of solute and solvent. Several approaches have been investigated, such as Snyder's well-known P' scale and the MOSCED scale from Eckert. However, most of the models are only valid for a certain subsets of chemicals. The complexity of molecular interaction leads to much more complicated models, such as the linear solvation energy relationship (LSER) and the quantitative structure-retention relationships (QSRRs). Still, these approaches fail to predict the retention of peptides, especially the sequence shuffled peptide sets, peptide enantiomers and diastereomers.

Therefore, there is a need for improvement of chromatographic purification.

SUMMARY OF THE INVENTION

One aspect of the present invention is a method of identifying, quantifying, or purifying a compound from a mixture through a chromatographic column loaded with a column adsorbent. The method comprises:

applying the mixture to the chromatographic column;
eluting the mixture with an elution solvent composition; and
collecting the compound;
wherein at least one of the column adsorbent and elution solvent is selected based on one of solubility parameters of the compound, column adsorbent, elution solvent, and conformation energy of the compound.

In accordance with an embodiment of the present invention, at least one of the column adsorbent and eluting solvent composition is selected based on the following steps:
a) identifying a critical pair composed of the compound and an impurity;
b)
1. if structure difference between the critical pair is substantial,
  b.1.a) selecting at least one of the column adsorbent and elution solvent composition so that $R_A$ is substantially away from 1, wherein $R_A$ is defined as following $$R_\Delta = \frac{(\Delta\delta)^2_{API\text{-}L} - (\Delta\delta)^2_{API\text{-}S}}{(\Delta\delta)^2_{I\text{-}L} - (\Delta\delta)^2_{I\text{-}S}}$$

which $(\Delta\delta)^2_{API\text{-}L}$ is the total solubility parameter difference between compound (API) and resin (L) in a square; $(\Delta\delta)^2_{API\text{-}S}$ is the total solubility parameter difference between API and elution solvent(S) in a square; $(\Delta\delta)^2_{I\text{-}L}$ is the total solubility parameter difference between impurity (I) and resin in a square; and $(\Delta\delta)^2_{I\text{-}S}$ is the total solubility parameter difference between I and elution solvent.
  b.1.b) separating the compound;
  b.1.c) if a baseline separation is not achieved in step b.1.b), continuing selecting at least one of the column adsorbent and elution solvent composition so that the $R_A$ is greater than 1.05 or less than 0.95;
2) if structure difference between the critical pair is insubstantial,
  b.2.a) selecting the elution solvent composition so that solution conformation energy difference between the critical pair is larger than 0.2 kcal/mole;
  b.2.b) separating the compound; and
  b.2.c) if a baseline separation is not achieved in step b.2.b), then continuing selecting the elution solvent composition so that the solution conformation energy difference between the critical pair is larger than 0.2 kcal/mole.

The compound to be purified may be a peptide.
The column adsorbent may be a resin.
As a preferred embodiment, the column adsorbent is selected based on the solubility parameters of dispersion ($\delta_d$), polarity ($\delta_p$), and hydrogen bonding ($\delta_h$).

In accordance with another preferred embodiment, the elution solvent composition is selected from tuning the solubility parameters of dispersion ($\delta_d$), polarity ($\delta_p$), and hydrogen bonding ($\delta_h$).

The conformation energy may be obtained from molecular dynamics simulation.

The chromatographic column is preferably a reversed-phase chromatographic column.

The steps b1.a) and b1.c) discussed above may be conducted so that $R_A$ is greater than 2 or less than 0.7, more preferably greater than 5 or less than 0.5.

The steps b2.a) and b2.c) discussed above may be conducted so that the solution conformation energy difference between the critical pair is larger than 20 kcal/mole.18, more preferably larger than 40 kcal/mole.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

Definitions

Figure 1:
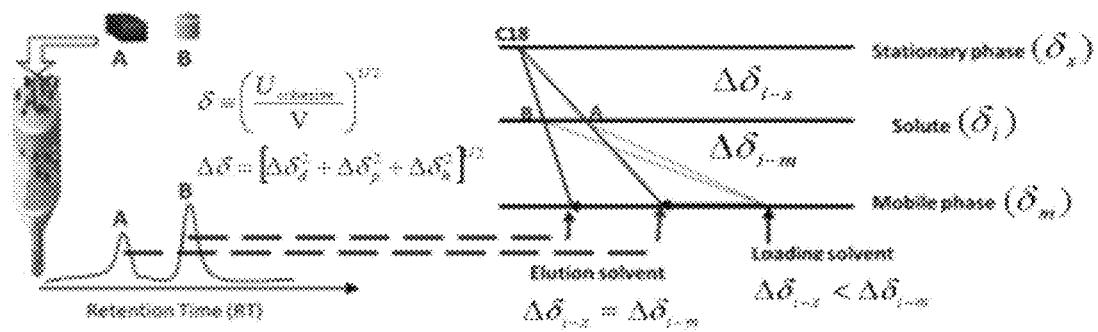
FIG. 1 provides a new strategy for better peptide purification by HPLC.

The following definitions apply to some of the elements described with respect to some embodiments of the invention. These definitions may likewise be expanded upon herein.

As used herein, the term "solubility parameter" refers to an index for predicting whether one material will dissolve in another and form a solution.

As used herein, the term "solubility parameters of dispersion ($\delta_d$)" refers to the energy from dispersion forces between molecules.

As used herein, the term "solubility parameters of polarity ($\delta_p$)" refers to the energy from dipolar intermolecular force between molecules.

As used herein, the term "solubility parameters of hydrogen bonding ($\delta_h$)" refers to the energy from hydrogen bonds between molecules.

As used herein, the term "molecular dynamics (MD) simulation" refers to a computer simulation of physical movements of atoms and molecules. Implicit solvent MD simulation indicates that the simulation system without adding any solvent such as water molecules and ACN molecules, etc.

As used herein, the term "elution solvent" refers to the solvent in mobile phase.

As used herein, the term "solid phase" refers to an adsorbent, such as a gel or resin, in the column.

As used herein, the term "chromatography" refers to widely used analysis of various chemical substances. It is a collective term for a set of laboratory techniques for separation of mixtures. The mixture is dissolved in a fluid called the "mobile phase", which carries the mixture through the packed resins (stationary phase). The various components of the mixture travel at different speeds in column, causing them to separate. The separation is based on differential partitioning between the mobile and stationary phases. Subtle differences in a compound's partition coefficient result in differential retention on the stationary phase and thus changing the separation.

As used herein, the term "retention factor" describes the migration rate of an analyte on a column, which is defined as following equation:

$$k' = \frac{t_R - t_0}{t_0}$$

where $t_R$ and $t_0$ are the retention time of peptide and non-retained molecule in RPC column, respectively.

As used herein, the term "baseline separation" refers to separation of multiple components, such as binary- or three-components with the peaks of the components not overlapping with each other.

As used herein, R$_\Delta$ is defined as following $$R_\Delta = \frac{(\Delta\delta)^2_{API-L} - (\Delta\delta)^2_{API-S}}{(\Delta\delta)^2_{I-L} - (\Delta\delta)^2_{I-S}}$$

wherein $(\Delta\delta)^2_{API-L}$ is the total solubility parameter difference between compound (API) and resin(L) in a square; $(\Delta\delta)^2_{API-S}$ is the total solubility parameter difference between API and elution solvent(S) in a square; $(\Delta\delta)^2_{I-L}$ is the total solubility parameter difference between impurity(I) and resin in a square; and $(\Delta\delta)^2_{I-S}$ is the total solubility parameter difference between I and elution solvent.

A person of ordinary skill in the art will be able to readily understand the meaning that R$_\Delta$ is significantly, substantially, or far away from 1. For example, R$_\Delta$ may be greater than 1.05, preferably greater than 2, and more preferably greater than >5 or less than 0.95, preferably less than 0.7, and more preferably less than 0.5.

As used herein, the term "solution conformation energy" refers to the total conformation energy of solute in its dissolved solvent. The energy is the sum of bond, angle, dihedral, hydrogen bond, van der Waals (VDW) and electrostatic energies.

As used herein, the term "critical pair" refers to a compound to be purified (e.g., API) and an impurity with similar chemical structure or physical properties, such as hydrophobicity and charge distribution. The critical pair are eluted in almost the same elution time (the peaks of components are overlapping in chromatogram) under some chromatographic conditions.

In accordance with the present invention, a person of ordinary skill in the art will be able to determine when the structural difference between a critical pair is substantial based on the sprit and scope of the present invention and any available means, such as CD spectrum. For example, when the differential CD spectra ($\Delta\theta$) between a critical pair (e.g., an API and an impurity) from 200 nm to 250 nm is within the range from 0 to 5000 (cm$^2$ mol$^{-1}$ degree), then the structure difference between the critical pair is deemed insubstantial. When the differential CD spectra($\Delta\theta$) is above 5000 cm$^2$ mol$^{-1}$ degree, then the structure difference between the critical pair is deemed substantial.

As used herein, the term "sample loading solvent" refers to a solvent which is used to dissolve the sample.

In biochromatographic separation, it's critical to properly select elution solvent, sample solvent and resin for obtaining the high purity and yield of active pharmaceutical ingredient (API), especially for the peptide drug. The present invention highlighted significant terms of how to rationally choose the elution solvent, sample loading solvent composition and column resin for optimizing the purification process by reversed-phase chromatography (RPC). The retention behaviors of API and impurities were dominated by the interaction difference between hydrophobic resin and elution solvent. Most studies have usually used the hydrophobicity index to predict the retentions of API and impurities. However, the solubility parameter provides a detail molecular/atomic interaction by dividing into three energies, that is, polarity, dispersion and hydrogen bonds. Based on this consideration, the present invention could accurately choose the solvent and resin to control the retention of API and impurities to optimize the appropriate separation condition. However, the solubility parameter estimation for API and its diastereomers separation would fail arising from the same solubility parameter of them. Hence, the present invention applies structure information on how to solve the chromatographic separation problem of peptide diastereomers, even for the enantiomers. Molecular dynamics simulation (MD) could provide the conformational information of API and its diastereomers. The order of the conformation energies of peptides in solution could be used to predict their retention order in RPC. The present invention proved that the conformation energies of peptide diastereomers in solution could well predict the retention behaviors of API and its diastereomers in RPC. Through the calculations of solubility parameter of peptide, resin, solvent composition and conformation energy of peptide in elution solvent, the present invention proposed an effective separation procedure for API and its impurities by RPC.

The present invention proposed the schemes (FIGS. 1 and 2) on optimizing the purification process of API and impurities, even for diastereomers/enantiomeric impurities. As illustrated in FIG. 1, the difference between the solutes', the column's and the solvents' solubility is chosen to manipulate the elution behavior of the solutes. The solubility parameters of resin and solvent could also be obtained by the experimental determination or Hensen table. Taking the separation of API (component A) and impurity (component B) by reversed-phase chromatography as an example, the elution condition of A and B started from a lower elution strength solvent to higher one. Initially, the $\Delta\delta_{A-R}$ ($\delta_{component\ A}$-$\delta_{resin}$) is larger than $\Delta\delta_{A-m}$ ($\delta_{component\ A}$-$\delta_{mobile\ phase\ 0}$) and $\Delta\delta_{B-R}$ ($\delta_{component\ B}$-$\delta_{resin}$) is larger than $\Delta\delta_{B-m}$ ($\delta_{component\ B}$-$\delta_{mobile\ phase\ 0}$). If the solubility parameter of $\Delta\delta_{A-R}$ is equal to $\Delta\delta_{A-m}$ ($\delta_{component\ A}$-$\delta_{mobile\ phase\ 1}$), the component A could be eluted with the elution solvent 1. Then, the B component could be eluted with increasing the elution solvent 2 and at the same time the solubility parameter of $\Delta\delta_{B-R}$ is equal to $\Delta\delta_{B-m}$ ($\delta_{component\ B}$-$\delta_{mobile\ phase\ 2}$).

Figure 2:
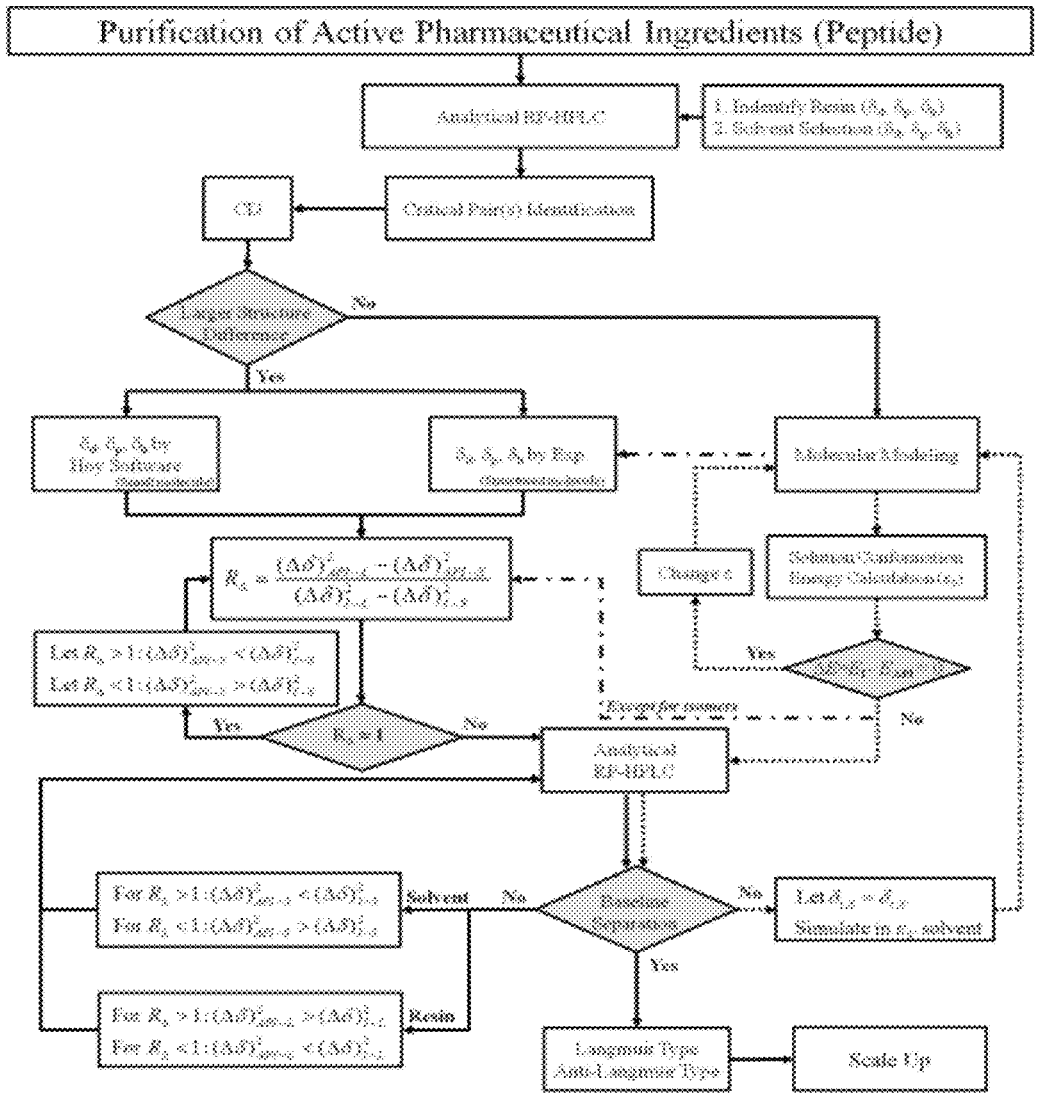
FIG. 2 provides the purification process of active pharmaceutical ingredient (API) and impurities.

As illustrated in FIG. 2, the solubility parameter of API could be calculated by group contribution methods (Hoy software or Hensen table), or determined by experimental measurement. The solubility parameter of column could also be obtained from the experimental determination. Besides, the solubility parameter of the different mobile phase compositions could be calculated by the mixing rule. Then, the analytical columns were used to pre-separate the API and impurities with the proper resins and elution solvents, which are based on the solubility parameter theory. In detail, the separation and purification schemes could be divided into three parts.

First, the impurities should be characterized and found the critical pair(s) in pre-separation step. The API and impurities should be identified by MS-MS or NMR, to name a few. CD spectra of API and impurities were determined to obtain the structure information, which was a critical check point in FIG. 2, in particular, as the impurities were the isomers including the sequence positional isomer, diasteriomers and enantiomers.

For the structure difference between the critical pair is substantial, the relative separation index (RΔ) was directly used to select the proper solvent, which was based on the ratio of the solubility difference between API-resin and API-solvent to that of impurity-resin and impurity-solvent. If the solvent composition chosen would let the RΔ to be close to 1, the solvent composition should be changed to let the RΔ far away from 1, then used this solvent composition to check whether the critical pair is separated with baseline separation. If it doesn't work, try to select another solvent or resin by the criterion of RΔ far away from 1.

On the other hand, we used the molecular simulation to calculate the solution conformation energies of critical pair for insubstantial structure difference set of critical pair(s). The present invention proved that the larger solution conformation energy difference of critical pair would let the critical pair to be separated well. Therefore, a proper solvent composition should be chosen to achieve the larger energy difference between API and impurity. Here, the solvent composition was determined by the dielectric constant; however, the conformation energy of critical pair in dielectric medium could be easily obtained. If the energy difference of critical pair in dielectric medium is too small, another dielectric medium should be changed. The criterion was based on the same elution strength but different in the dielectric medium. Because if the elution strength was changed, the elution behavior might be changed. The same elution strength like that the strength of 55% ACN/H$_2$O was the same as the 32% THF, but the dielectric constant was different resulting in different conformation of solute in dielectric medium. As mention above, it has to further check whether the critical pair was baseline separation by proper dielectric medium.

Finally, if an optimal condition could be tuned for the critical pair(s) separation in analytical column, then the API could be purified in large scale. Based on this Figure, the present invention has successfully achieved the based-line separation of critical pair(s) in RPC operation.

EXAMPLES

Three Exenatide diastereomers were designed by 11$^{th}$, 32$^{nd}$ and 39$^{th}$ serine residue being individually racemized with a single amino acid to D-form. To understand the structure-retention relationship of Exenatide and its diastereomers in RPC, solution conformation information of peptide was determined by CD spectra as well as MD simulation and the retention behaviors were monitored by RP-HPLC with isocratic elution. Solution structural stability of peptide was obtained through the help of solution conformation energy calculation of which was assisted by implicit solvent MD simulation. Based on the structure-retention relationship, the rational strategy for the optimized separation of peptide diastereomers by RPC was examined.

Example 1

CD Spectra of Exenatide and its Diastereomers in Aqueous Phase

Figure 3:
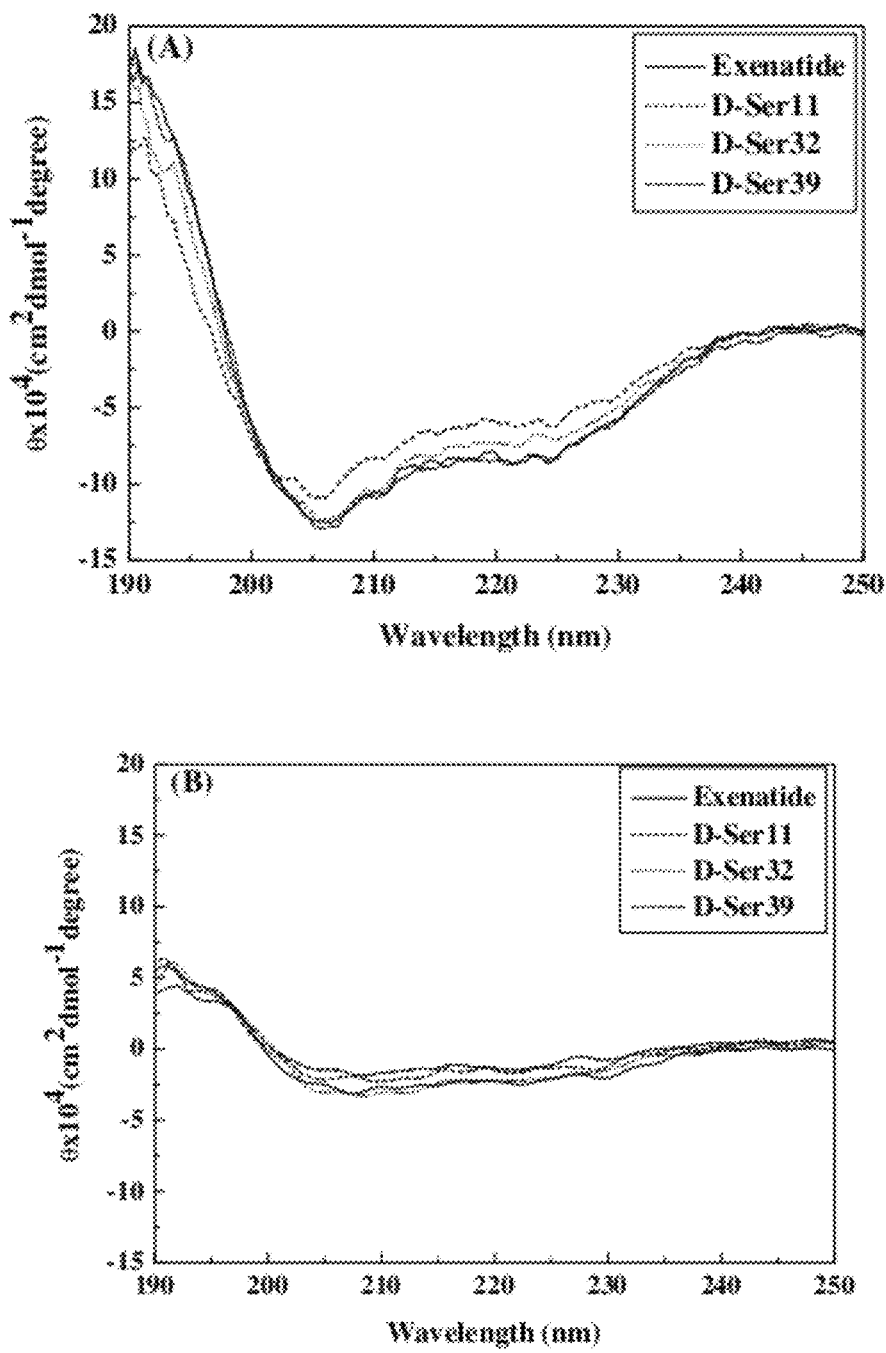
FIG. 3 provides the circular dichroism spectra of Exenatide and its diastereomers in aqueous solution. (A) 0% ACN/H$_2$O and (B) 36% ACN/H$_2$O.

Secondary structures of Exenatide and its diastereomers in aqueous solution were monitored by CD spectrometer. FIG. 3

(A) showed the spectra of these peptides in 0% ACN/H$_2$O containing of 0.1% TFA. All peptides exhibited an alpha-helical structure resulting from the characteristic negative peak at 222 nm. The structure of D-Ser39 substitution was almost identical to the native Exenatide because of the racemization at the end of Exenatide. In contrast, the helicities of the D-Ser11 and D-Ser32 peptides were lower than that of Exenatide due to the D-form mutation near the middle of peptide, which the helicity would be destroyed. On the other hand, the CD spectra of Exenatide peptide and its diastereomers in 36% ACN/H$_2$O solution containing of 0.1% TFA were shown in FIG. 3 (B). In 36% ACN/H$_2$O solution, the helical structures of all peptide were almost fully unfolding; and the structural discrepancy of all D-form diastereomers was observed.

Example 2

Retention Behaviors of Exenatide and its Diastereomers in RP-HPLC

Figure 4:
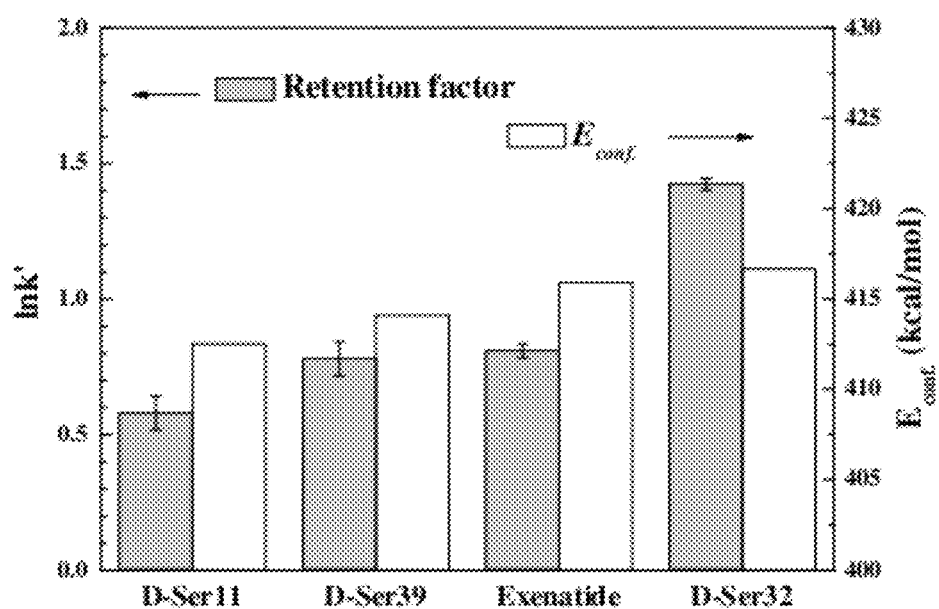
FIG. 4 provides the solution conformation energy (E$_{conf.}$) in 36% ACN/H$_2$O and the retention factor (lnk') of Exenatide and its diastereomers in RPC.
Figure 5:
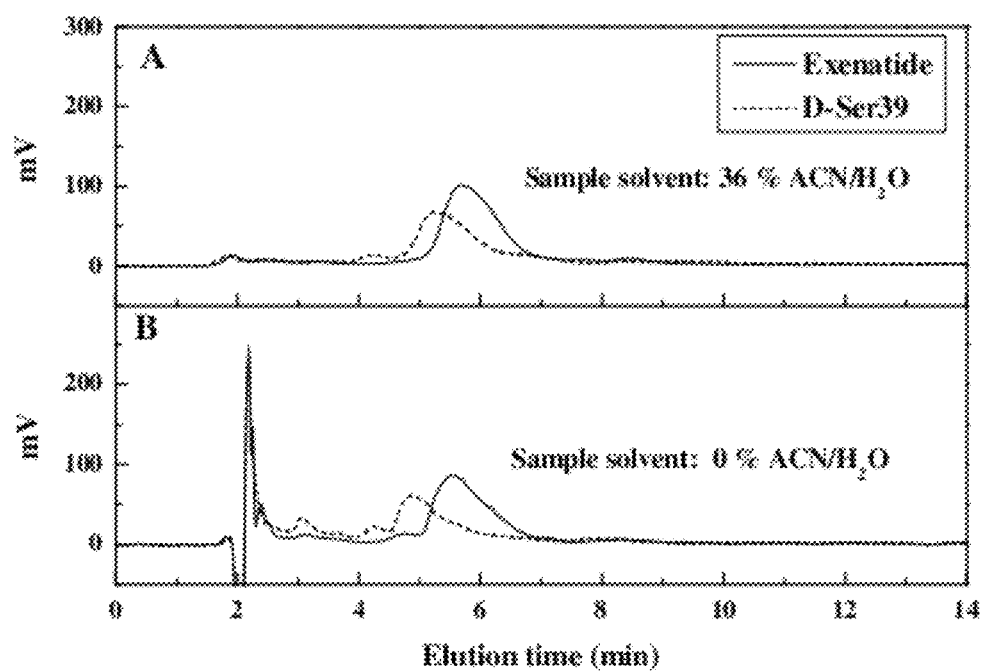
FIG. 5 provides the chromatograms of Exenatide and its diastereomers in RP-HPLC. The peptide was eluted by 36% ACN/H$_2$O containing of 0.1% TFA with the flow rate of 1 mL/min at 25° C. (A) The sample loading solvent is the same as the elution solvent; (B) The sample loading solvent is 0% ACN/H$_2$O containing of 0.1% TFA.

The retention behaviors of Exenatide and its diastereomers in RPC column were examined using the isocratic elution of 36% ACN/H$_2$O containing of 0.1% TFA at 25° C. As shown in FIG. 4, the retention order of these peptides followed by D-Ser32>Exenatide≈D-Ser39, and the D-Ser11 was less retained. Apparently, Exenatide and D-Ser39 formed a critical pair under this chromatographic operation condition. In fact, these peptide diastereomers have identical hydrophobicity according to the residue-based hydrophobicity scale (Table 1) but the retention factors were different. In addition, the sample loading solvent effect on the retention behavior of the critical pair was investigated. Exenatide and D-Ser39 were dissolved in 0% ACN/H$_2$O containing of 0.1% TFA, and the retention behaviors of these peptides in C18 column were performed with the isocratic elution of 36% ACN/H$_2$O. The chromatograms were shown in FIG. 5. The result revealed that the peaks of Exenatide and D-Ser39 were slightly separated as the sample loading solvent changed from 36% to 0% ACN/H$_2$O solution. In this case, adsorption between peptide and hydrophobic ligand was considered an equilibrium state. If the sample solvent was different from elution solvent, the initial association between peptide and hydrophobic resin would be affected. Thus, the sample loading solvent effect seemed to influence the retention behavior of peptide, and promoted the separation of the critical pair of Exenatide and D-Ser39.

Example 3

MD Simulations of Exenatide and its Diastereomers in Aqueous Solution

Figure 6:
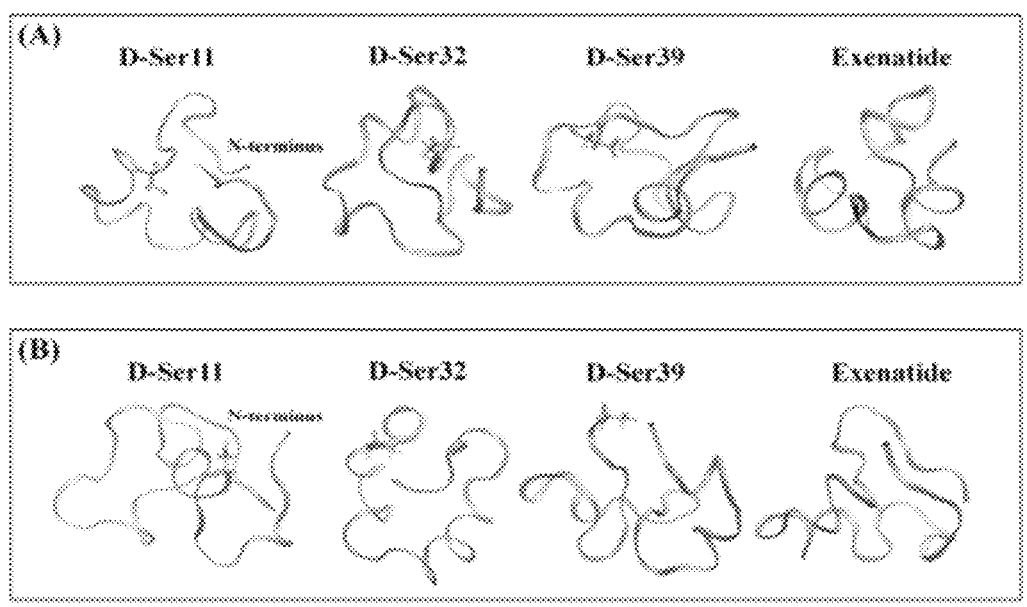
FIG. 6 provides the snapshots of Exenatide and its diastereomers by implicit solvent MD simulation at 1 ns. Solution structures of peptide in (A) 0% ACN/H$_2$O and (B) 36% ACN/H$_2$O were shown. Serine residue with D-form substitution was represented by stick bond, and the peptide was represented by ribbon.

Implicit solvent MD simulations were performed to determine the solution structure as well as the solution conformation energy. Each modeling system was carried out for 1 ns. The structures of all peptides in 36% ACN/H$_2$O were considered to be equilibrated at the least 0.2 ns according to the root mean square deviation within 2 Å. In the operation condition of RPC, the solvent usually contained of 0.1% TFA to eliminate the electrostatic force between the solute and hydrophobic resin. All peptides were constructed with the charged amino acids being protonated in each simulation system. Thus, the solution structure of Exenatide might be different from the NMR solved structure. FIGS. 6 (A) and (B) showed the snapshot of Exenatide and its diastereomers in 0 and 36% ACN/H$_2$O at 1 ns, respectively. As our expectation, simulation structure of Exenatide in 0% ACN/H$_2$O was different from NMR solved structure. And the helical structure of Exenatide was noticeably destructed in 36% ACN/H$_2$O solution. This was consistent with the CD spectra. For D-form substituted peptide, similar results were observed that the structure deformation occurs with the increase concentration of ACN in solution. Furthermore, the solution conformation energy of Exenatide and its diastereomers was calculated. By comparison with retention factor (FIG. 4), it could be found that the most retained D-Ser32 peptide owned the highest solution conformation energy in the simulation system of peptide in 36% ACN/H$_2$O. Besides, the retention order of these peptide diastereomers was the same as the order of solution conformation energy. Otherwise, MD simulations of two peptide diastereomers of which the less retained peptide (LALA-R-ELEELN, R=L-Arg (SEQ ID NO: 5)) and the more retained one (LALA-r-ELEELN, r=D-Arg (SEQ ID NO: 6)) were also performed. The elution solvent composition is based on the chromatogram from Winter et al. (*Journal of Separation Science*, 2009, 32, 1111). The solution conformation energies of D-Arg peptide and L-Arg were 138.99 and 135.75 kcal/mol, respectively. The energy calculation was also fitting with the retention behavior prediction. Therefore, the solution conformation energy of peptide diastereomers indeed could be applied in the retention behavior prediction.

Moreover, it's found that the Exenatide and D-Ser39 could be slightly separated by changing the sample solvent from

TABLE 1

The sequence of exenatide peptide and its diastereomers

| Peptide | Sequence[a] | Hydrophobicity[b] (kcal/mol) |
| --- | --- | --- |
| Exenatide | H-HGEGTFTSDLSKQMEEEAVRLFIEWLKNGGPSSGAPPPS-NH$_2$ (SEQ ID NO: 1) | 8.72 |
| D-Ser11 | H-HGEGTFTSDLSKQMEEEAVRLFIEWLKNGGPSSGAPPPS-NH$_2$ (SEQ ID NO: 2) | 8.72 |
| D-Ser32 | H-HGEGTFTSDLSKQMEEEAVRLFIEWLKNGGPSSGAPPPS-NH$_2$ (SEQ ID NO: 3) | 8.72 |
| D-Ser39 | H-HGEGTFTSDLSKQMEEEAVRLFIEWLKNGGPSSGAPPPS-NH$_2$ (SEQ ID NO: 4) | 8.72 |

[a]One-letter amino acid core is used; underline residue represents the D-amino acid, and the peptides used were amidated at the C-terminus.
[b]The hydrophobicity is obtained from Wimley and White (1996).

36% to 0% ACN/H$_2$O. Accordingly, the MD simulations of Exenatide and D-Ser39 in 0% ACN/H$_2$O were performed to calculate the solution conformation energy. The results revealed that the solution conformation energies of Exenatide and D-Ser39 are 415.75 and 412.91 kcal/mol, respectively. Comparison with the retention behaviors of Exenatide and D-Ser39 using 0% ACN/H$_2$O as the sample loading solvent, it's found that Exenatide in 0% ACN/H$_2$O sample loading solvent owns larger solution conformation energy resulting in longer retention time. In contrast, D-Ser39 has lower solution conformation energy would be less retained. On the other hand, the solution conformation energy difference of these peptides in 0% ACN/H$_2$O is larger than those of them in 36% ACN/H$_2$O resulting in slight separation. Interestingly, the solution conformation energy of Exenatide in 36% ACN/H$_2$O sample loading solvent is larger than that of Exenatide in 0% ACN/H$_2$O sample loading solvent, so does the behaviors of D-Ser39 peptide. It's found that the retention time of these two peptides in 36% ACN/H$_2$O sample loading solvent are longer than those of them in 0% ACN/H$_2$O sample loading solvent. These results are corresponding to the retention behaviors in RPC based on our proposed structure-retention relationship. Hence, it's inferred that the tuning of sample loading solvent which contributes to enlarge the difference of solution conformation change would facilitate the diastereomer separation. Also, it could be applied to the elution solvent change. Moreover, the difference of solution conformation energy in 0% and 36 ACN/H$_2$O sample loading solvent is too small to achieve the baseline separation. Thus, the further approach could be performed by tuning the composition of elution solvent.

Example 4

Critical Pair Separation by Elution Solvent Tuning

Figure 8:
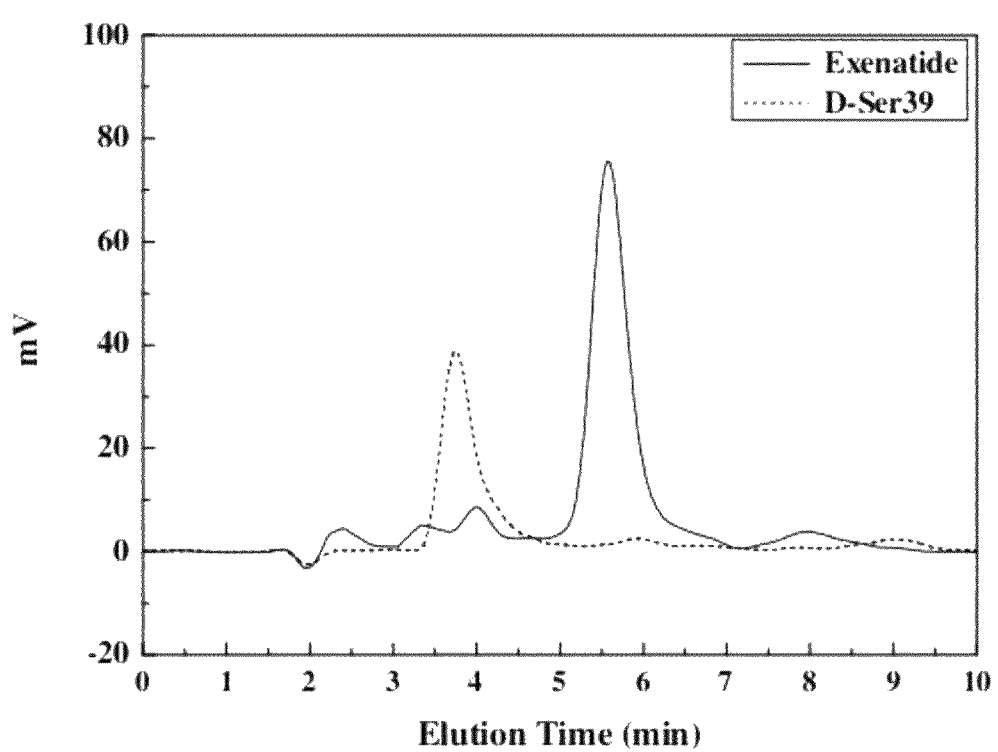
FIG. 8 provides the chromatogram of the critical pair separation which was eluted isocratically by 32% THF/H$_2$O containing of 0.1% TFA.

The critical pair of Exenatide and D-Ser39 peptide was observed from both simulation prediction and the chromatograms. Even though the sample loading solvent composition was changed, the critical pair was still present. Thus, we tried to change the elution solvent to mediate the solution conformation difference of this critical pair. Before we selected a proper solvent for the critical pair separation, we calculated the solution conformation energy by performing the MD simulation using the dielectric constant of 55.75, which is corresponding to ca. 55% ACN/H$_2$O solution as well as 32% THF/H$_2$O mixing solution. However, the difference of solution conformation energy between this critical pair in 55% ACN/H$_2$O solution is 2.98 kcal/mol, which is larger than that of in 0% ACN/H$_2$O. Unfortunately, the critical pair is not retained by 55% ACN/H$_2$O elution. Therefore, we intended to find the other solvent of which dielectric constant equals to 55% ACN/H$_2$O, but the elution strength is lower than 55% ACN/H$_2$O. One of the solvent compositions is 32% THF/H$_2$O. The CD spectrum of Exenatide in 32% THF/H$_2$O is identical to that of Exenatide in 55% ACN/H$_2$O, so does the CD spectrum of D-Ser39 peptide. Therefore, we assumed that the conformation energy of Exenatide in 32% THF/H$_2$O is the same as Exenatide in 55% ACN/H$_2$O. Similarly, the conformation energy of D-Ser39 in 32% THF/H$_2$O is the same as D-Ser39 in 55 ACN/H$_2$O. In our case, the structural stability is related to the dielectric constant of solvent and not strongly affected by solvent species. FIG. 8 showed the chromatogram of Exenatide and D-Ser39; the result showed that this critical pair could be well separated under the 32% THF/H$_2$O mixing solution. Consequently, the baseline separation of Exenatide and D-Ser39 in RPC was successfully achieved by tuning the elution solvent.

Example 5

Structure Stability-Retention Relationship for Peptide Diastereomers Separation

Separation of critical pair which was produced from improper purification condition was significant in the field of peptide drug manufacture. RPC was extensively used in bioseparation according to its simple operation and higher resolution. P reposing a rational strategy for peptide diastereomers separation by chromatography was important and essential for pharmaceutical industry. In clinical application, the purity requirement of peptide drug was as high as 99.5% or greater. To approach this requirement, obtaining the optimal chromatographic condition in both analytical and even for preparative scales was necessary.

Figure 7:
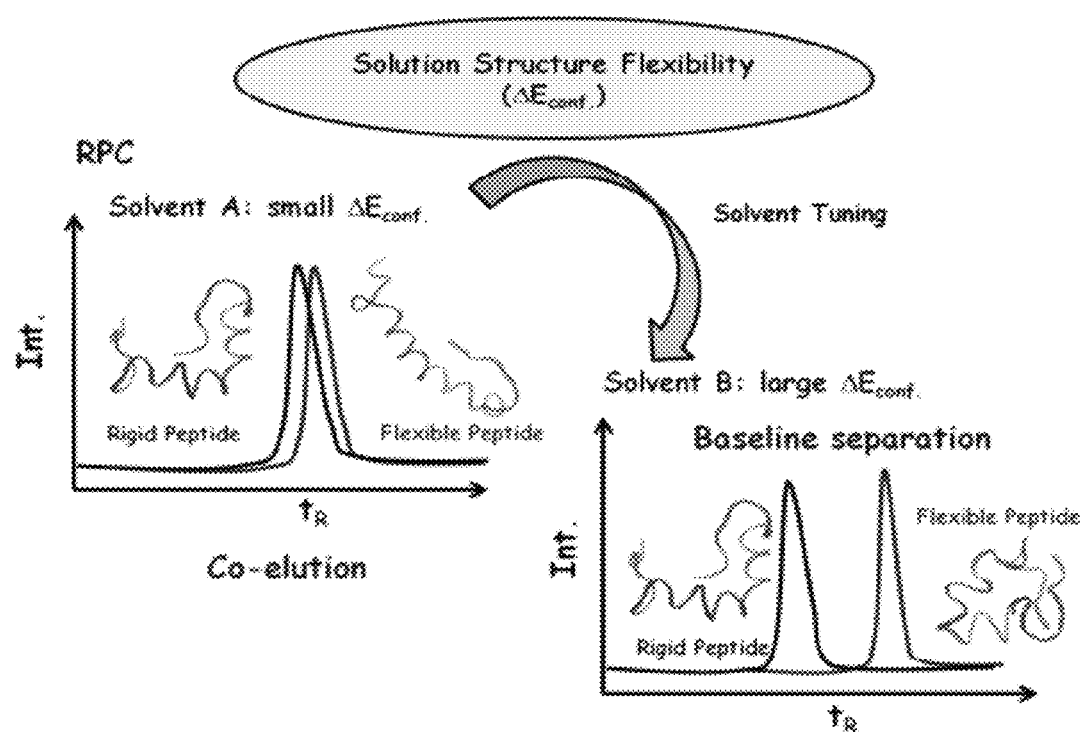
FIG. 7 provides the relationships between structural flexibility and retention behavior of peptide diastereomers along with the solvent tuning. These peptides in elution solvent A were co-eluted with the small difference of solution conformation energy and exhibited the baseline-separation with large difference of solution conformation energy in elution solvent B.

FIG. 7 showed relationships between the structural flexibility and retention behavior of peptide diastereomers. From MD simulation analysis and retention factor measurements, peptide diastereomer with higher solution conformation energy would exhibit larger retention factor. On the contrary, peptide diastereomer with lower solution conformation energy would exhibit lower retention factor. Therefore, it could be suggested that the solution structure stability should be critical on the retention behaviors. As mention from previous study, the peptide with rigid structure (small solution conformation energy) would not be easily deformed on the hydrophobic resin because of the unfavorable enthalpy loss. On the contrary, the flexible peptide (large solution conformation energy) with lower structural stability would be more favorable to adsorb onto the hydrophobic surface than the rigid one (*The Journal of Physical chemistry. B*, 2010, 114, 11620). The role of peptide structure flexibility in peptide diastereomers retention prediction evidenced in this invention was consistent with previous study for positional peptide isomers retention prediction: the more flexible peptide was more retained in C18-resin. Moreover, the solution conformation energy difference also facilitated the critical pair separation by RPC. The tuning of sample loading solvent or elution solvent with the solution conformation energy difference being larger would be resulting in the baseline separation of the critical pair.

Example 6

Optimization of the Critical Pair Separation

Base on the examination of structural stability-retention relationship, it should first obtain the solution structural stability difference of the critical pair by MD simulation of them in different aqueous solution. Then, choosing a proper sample loading solvent and elution solvent were based on the solution structural stability difference. Implicit MD simulations of Exenatide and D-Ser39 in 0, 36 and 55% ACN/H$_2$O solution were performed to obtain the solution structural stability difference of this critical pair. The solution conformation energy difference of the critical pair in 55% ACN/H$_2$O was larger than those of in 0% ACN/H$_2$O, and follows by 36% ACN/H$_2$O. This implied that it could use the 55% ACN/H$_2$O as the proper sample loading solvent for the critical pair separation. Nevertheless, this solvent strength of sample loading solvent was actually so strong that peptide wasn't easily retained in RPC. Another proper sample solvent of 0% ACN/H$_2$O was chosen resulting in the slight peak separation of critical pair, but the critical pair was still present. Accordingly, the elution solvent was further mediated. From simulation implication, the 55% and 0% ACN/H$_2$O solutions might be the proper candidates to be the elution solvent from the solution structural stability; however, the critical pair would be non-retained and non-eluted by these two elution solvents. Therefore, the change of the elution solvent was required to achieve the baseline separation of critical pair. MD simulation utilized a solvation force field to obtain the equilibrium structure in aqueous solution. The inventors assumed that the structure of peptide in the different solvent composition with the same dielectric medium might be almost the same. The dielectric medium of 55% ACN/H$_2$O is approximately equivalent to 32% THF/H$_2$O solution. Thus, the 32% THF/H$_2$O solution was took as the elution and sample loading solvent for the critical pair separation. This optimization procedure facilitated the baseline separation of the critical pair, Exenatide and D-Ser39. Consequently, the structural stability-retention relationship actually provides an important implication on peptide separation in RP-H PLC, especially for isomeric impurities.

What is claimed is:

1. A method of identifying, quantifying, or purifying a compound from a mixture through a chromatographic column loaded with a column adsorbent comprising:
   A) selecting at least one of the column adsorbent and eluting solvent composition by performing the following steps:
      a) identifying a critical pair composed of the compound and an impurity;
      b)
         1. if the differential CD spectra ($\Delta\theta$) from 200 nm to 250 nm between the critical pair is larger than 5000 $cm^2\ mol^{-1}$ degree,
            b.1.a) selecting at least one of the column adsorbent and elution solvent composition so that $R_A$ is greater than 1.05 or less than 0.95, wherein $R_A$ is defined as following:

$$R_\Delta = \frac{(\Delta\delta)^2_{API-L} - (\Delta\delta)^2_{API-S}}{(\Delta\delta)^2_{I-L} - (\Delta\delta)^2_{I-S}}$$

which $(\Delta\delta)^2_{API-L}$ is the total solubility parameter difference between compound (API) and resin(L) in a square; $(\Delta\delta)^2_{API-S}$ is the total solubility parameter difference between API and elution solvent(S) in a square; $(\Delta\delta)^2_{I-L}$ is the total solubility parameter difference between impurity(I) and resin in a square; and $(\Delta\delta)^2_{I-S}$ is the total solubility parameter difference between I and elution solvent;
            b.1.b) separating the compound;
            b.1.c) if a baseline separation is not achieved in step b.1.b), continuing selecting at least one of the column adsorbent and elution solvent composition so that the $R_A$ is greater than 1.05 or less than 0.95;
         2. if the differential CD spectra ($\Delta\theta$) between the critical pair from 200 nm to 250 nm is within the range from 0 to 5000 $cm^2\ mol^{-1}$ degree,
            b.2.a) selecting the elution solvent composition so that solution conformation energy difference between the critical pair is larger than 0.2 kcal/mole;
            b.2.b) separating the compound; and
            b.2.c) if a baseline separation is not achieved in step b.2.b), then continuing selecting the elution solvent composition so that the solution conformation energy difference between the critical pair is larger than 0.2 kcal/mole;
   B) applying the mixture to the chromatographic column;
   C) eluting the mixture with an elution solvent composition; and
   D) collecting the compound.

2. The method of claim 1, wherein the selecting step comprises selecting the column adsorbent based on the solubility parameters of dispersion ($\delta_d$), polarity ($\delta_p$), and hydrogen bonding ($\delta_h$).

3. The method of claim 1, wherein the selecting step comprises selecting the elution solvent composition by tuning the solubility parameters of dispersion ($\delta_d$), polarity ($\delta_p$), and hydrogen bonding ($\delta_h$).

4. The method of claim 1, wherein the conformation energy is obtained from molecular dynamics simulation.

5. The method of claim 1, wherein the chromatographic column is reversed-phase chromatographic column.

6. The method of claim 1 wherein the column adsorbent is resin.

7. The method of claim 1 wherein the compound is a peptide.

8. The method of claim 1 wherein the steps b1.a and b1.c are conducted so that $R_A$ is greater than 2 or less than 0.7.

9. The method of claim 1 wherein the steps b1.a and b1.c are conducted so that $R_A$ is greater than 5 or less than 0.5.

10. The method of claim 1 wherein the steps b.2.a) and b.2.c) are conducted so that the solution conformation energy difference between the critical pair is larger than 20 kcal/mole.

11. The method of claim 1 wherein the steps b.2.a) and b.2.c) are conducted so that the solution conformation energy difference between the critical pair is larger than 40 kcal/mole.

* * * * *